(12) United States Patent
Liu (10) Patent No.: US 12,004,597 B2
(45) Date of Patent: Jun. 11, 2024

(54) SHOE-PAD, SHOE AND HALLUX ORTHOTIC DEVICE

(71) Applicant: He Liu, Heilongjiang (CN)

(72) Inventor: He Liu, Heilongjiang (CN)

( * ) Notice: Subject to any disclaimer, the term of this patent is extended or adjusted under 35 U.S.C. 154(b) by 0 days.

(21) Appl. No.: 16/633,783

(22) PCT Filed: Apr. 9, 2019

(86) PCT No.: PCT/CN2019/081925
§ 371 (c)(1),
(2) Date: Jan. 24, 2020

(87) PCT Pub. No.: WO2020/042617
PCT Pub. Date: Mar. 5, 2020

(65) Prior Publication Data
US 2021/0361462 A1 Nov. 25, 2021

(30) Foreign Application Priority Data
Aug. 30, 2018 (CN) .......................... 201821417681.1

(51) Int. Cl.
*A43B 7/26* (2006.01)
*A43B 17/00* (2006.01)
*A61F 5/14* (2022.01)

(52) U.S. Cl.
CPC ............... *A43B 7/26* (2013.01); *A43B 17/00* (2013.01); *A61F 5/14* (2013.01)

(58) Field of Classification Search
CPC ...................................................... A43B 7/26
See application file for complete search history.

(56) References Cited

U.S. PATENT DOCUMENTS 2,506,308 A * 5/1950 Maynier ............... A61F 5/019
132/73
4,017,987 A * 4/1977 Perez, Jr. ............. A43B 3/105
36/94

(Continued)

FOREIGN PATENT DOCUMENTS

| CN | 202172914 U | 3/2012 |
| CN | 202179618 U | 4/2012 |

(Continued)

OTHER PUBLICATIONS

English Machine Translation to DE102014222239 Abstract.
(Continued)

*Primary Examiner* — Megan E Lynch
(74) *Attorney, Agent, or Firm* — CANTOR COLBURN LLP (57) ABSTRACT

A shoe-pad, shoe and hallux orthotic device, the shoe-pad is configured for correcting and preventing deformity of a hallux, the shoe-pad includes a shoe-pad body, a first orthotic portion, and a second orthotic portion; the first orthotic portion and the second orthotic portion are protruded from a surface of the shoe-pad body and spaced from each other, and the first orthotic portion and the second orthotic portion are staggered from each other in a front-back direction. The first orthotic portion and the second orthotic portion are spaced from each other on the shoe-pad body, and the first orthotic portion and the second orthotic portion are staggered from each other in a front-back direction, the structure is simple, the production and using are convenient, the hallux valgus can be corrected and prevented without a surgery, and the suffering and financial burden of the patients are reduced.

10 Claims, 9 Drawing Sheets

(56) References Cited

U.S. PATENT DOCUMENTS

| | | | | |
|---|---|---|---|---|
| 4,207,880 | A * | 6/1980 | Zinkovich | A43B 7/26 36/94 |
| D400,694 | S * | 11/1998 | Kang | D2/919 |
| 5,946,823 | A * | 9/1999 | Yates | A43B 7/26 36/94 |
| 8,769,846 | B1 * | 7/2014 | Williams | A43B 7/26 36/141 |
| 2007/0011915 | A1 * | 1/2007 | Allen | A43B 1/0081 36/94 |
| 2007/0074334 | A1 * | 4/2007 | Steel | A43B 7/26 36/9 R |
| 2008/0086918 | A1 * | 4/2008 | Chung | A61F 5/14 36/141 |
| 2008/0113854 | A1 * | 5/2008 | Ferri | A61F 5/019 482/148 |
| 2010/0263237 | A1 * | 10/2010 | Cuellar | A43B 3/24 132/73 |
| 2012/0330207 | A1 | 12/2012 | Goswami et al. | |
| 2013/0203556 | A1 * | 8/2013 | Ferri | A61F 5/019 482/79 |
| 2015/0297385 | A1 | 10/2015 | Tsai | |
| 2015/0374094 | A1 * | 12/2015 | Gift | A43B 23/081 36/94 |
| 2019/0029389 | A1 * | 1/2019 | Levy | A43B 3/12 |
| 2019/0240055 | A1 * | 8/2019 | Ferri | A63B 24/00 |

FOREIGN PATENT DOCUMENTS

| | | | |
|---|---|---|---|
| CN | 107072803 | A | 8/2017 |
| DE | 102014222239 | A1 | 5/2016 |
| FR | 794569 | A * | 2/1936 |
| JP | 2017121389 | A | 7/2017 |
| KR | 20120032093 | A * | 4/2012 |
| KR | 20120108527 | A * | 10/2012 |

OTHER PUBLICATIONS

English Machine Translation to CN202172914 Abstract.
English Machine Translation to CN202179618 Abstract.
English Machine Translation to CN107072803 Abstract.
English Machine Translation to JP2017121389 Abstract.
International Search Report for Application No. PCT/CN2019/081925.

* cited by examiner

SHOE-PAD, SHOE AND HALLUX ORTHOTIC DEVICE

CROSS REFERENCE TO RELATED APPLICATIONS

This application is the International Application No. PCT/CN2019/081925 for entry into US national phase, with an international filing date of Apr. 9, 2019 designating the U.S., and claims priority benefits to Chinese Patent Application No. CN201821417681.1, filed on Aug. 30, 2018, the contents each of which being incorporated herein by reference.

TECHNICAL FIELD

The present application relates to technical field of health care, and more particularly to a shoe-pad, a shoe and a hallux orthotic device.

BACKGROUND TECHNOLOGY

Hallux valgus is a common foot disease, and the risk of developing the hallux valgus increases with age. The production and development of hallux valgus is closely related to external factors. Wearing narrower or stiffer shoes will cause the back of the hallux and the first metatarsal to be backlogged and rubbed, resulting in or aggravating hallux valgus, which seriously affects the life quality of the patients.

The inventor of the present application has found in long-term research and development that the hallux valgus can currently be corrected by surgery, but the normal tissue structure of the foot will be destroyed, the healing speed is slow, there is a risk of infection, and the cost is high.

SUMMARY

The present application provides a shoe-pad, in order to solve the technical problem that the correcting and preventing of hallux valgus is difficult in the prior art.

In order to solve the above technical problem, the present application adopts a technical solution is to provide a shoe-pad, the shoe-pad configured for correcting and preventing deformity of a hallux and including:

a shoe-pad body;
a first orthotic portion; and
a second orthotic portion;

the first orthotic portion and the second orthotic portion are protruded from a surface of the shoe-pad body and spaced from each other, and the first orthotic portion and the second orthotic portion are staggered from each other in a front-back direction.

The hallux comprises a first bone portion, a second bone portion, and a third bone portion located from top to bottom, a first joint is formed between the first bone portion and the second bone portion, a second joint is formed between the second bone portion and the third bone portion, and the first orthotic portion and the second orthotic portion respectively correspond to the an outer side of the first joint and an inner side of the second joint.

A front end of the second orthotic portion is aligned with the second joint.

The first orthotic portion is provided with curved surfaces or oblique surfaces matching with the corresponding hallux and a second toe, and the second orthotic portion is provided with a curved surface or an oblique surface matching with the corresponding hallux.

A central axis of the first orthotic portion and a central axis of the second orthotic portion are not parallel, and projections of the first orthotic portion and the second orthotic portion on a width direction of the second orthotic portion are not overlapped.

The shoe-pad further comprises a third orthotic portion protruding from the surface of the shoe-pad body and spaced from the first orthotic portion, and the third orthotic portion is configured to correspond to an outer side of a second toe, a third toe and/or fourth toe.

The shoe-pad further comprises a recessed portion disposed on the surface of the shoe-pad body, and the recessed portion is configured to correspond to the hallux or other toes.

At least a part of the first orthotic portion or the second orthotic portion extends into an inside of the shoe-pad body, the shoe-pad comprises an adjusting portion disposed at a side of the shoe-pad body, and is connected with the part of the first orthotic portion or the second orthotic portion extended into the inside of the shoe-pad body.

In order to solve the above technical problem, the present application adopts another technical solution is to provide a shoe, configured for correcting and preventing deformity of a hallux, wherein the shoe comprises a first orthotic portion and a second orthotic portion protruding from a surface of a first pad and spaced from each other, and the first orthotic portion and the second orthotic portion are staggered from each other in a front-back direction.

In order to solve the above technical problem, the present application adopts a further technical solution is to provide a hallux orthotic device, wherein the hallux orthotic device is configured for correcting and preventing deformity of the hallux, and the hallux orthotic device comprises a first orthotic portion and a second orthotic portion protruding from a surface of a first pad and spaced from each other, and the first orthotic portion and the second orthotic portion are staggered from each other in a front-back direction.

In the present application, the first orthotic portion and the second orthotic portion are spaced from each other on the shoe-pad body, and the first orthotic portion and the second orthotic portion are staggered from each other in a front-back direction, the structure is simple, the production and using are convenient, the hallux valgus can be corrected and prevented without a surgery, and the suffering and financial burden of the patients are reduced.

BRIEF DESCRIPTION OF THE DRAWINGS

In order to explain the embodiments of the present application more clearly, a brief introduction regarding the accompanying drawings that need to be used for describing the embodiments of the present application or the prior art is given below; it is obvious that the accompanying drawings described as follows are only some embodiments of the present application, for those skilled in the art, other drawings can also be obtained according to the current drawings on the premise of paying no creative labor.

DETAILED DESCRIPTION

In the following, the technical solutions in the embodiments of the present application will be clearly and completely described with reference to the drawings in the embodiments of the present application. Obviously, the described embodiments are only a part of the embodiments of the present invention, not all of the implementation example. Based on the embodiments of the present application, all other embodiments obtained by those skilled in the art without creative labor shall fall within the protection scope of the present application.

The hallux valgus of the toes is a common foot disease, and more than 50% of them are natural. The solution of the present application can make the toes be corrected and plasticized from the beginning when walking.

In addition, the orthotic device of the present application can also be used for auxiliary recovery after surgery. Setting the orthotic device on the shoe-pad or shoes can play a very important role in the development and growth of the foot and the directional shaping.

Figure 1:
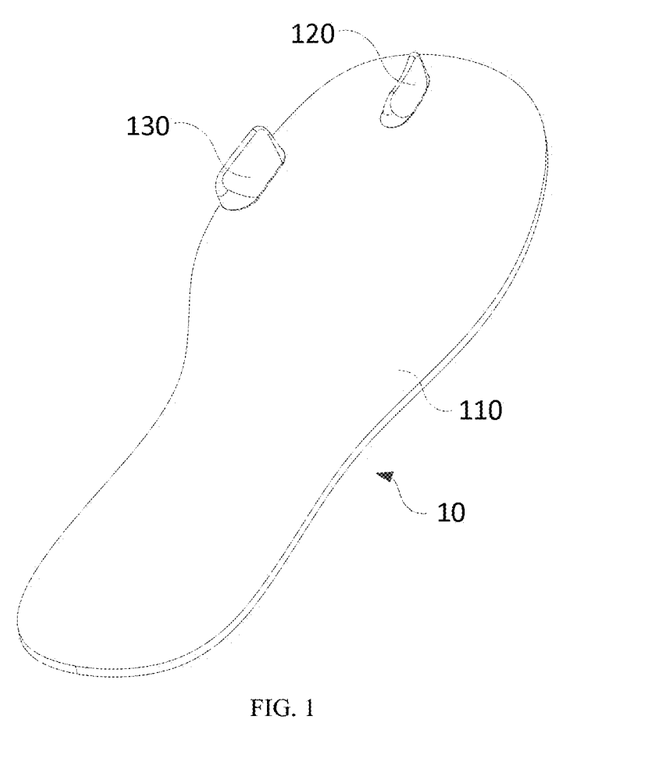
FIG. 1 is a schematic structural view of an embodiment of a shoe-pad of the present application.

Referring to FIG. 1, an embodiment of the shoe-pad 10 according to the present application includes a shoe-pad body 110 and a first orthotic portion 120 and a second orthotic portion 130, the first orthotic portion 120 and the second orthotic portion 130 are protruded from a surface of the shoe-pad body 110 and spaced from each other, and the first orthotic portion 120 and the second orthotic portion 130 are staggered from each other in a front-back direction, the shoe-pad 10 is configured for correcting and preventing deformity of the hallux. In this embodiment, the first orthotic portion 120 and the second orthotic portion 130 are integrally formed on the shoe-pad body 110. In other embodiments, the first orthotic portion 120 and the second orthotic portion 130 may also be fixedly connected to the shoe-pad body 110 by means of pasting or the like.

In this embodiment, the first orthotic portion 120 and the second orthotic portion 130 may be made of a polymer material, such as PU (Polyurethane, polyurethane), or EVA (Ethylene-Vinyl Acetate copolymer, ethylene-vinyl acetate copolymer).

Figure 2:
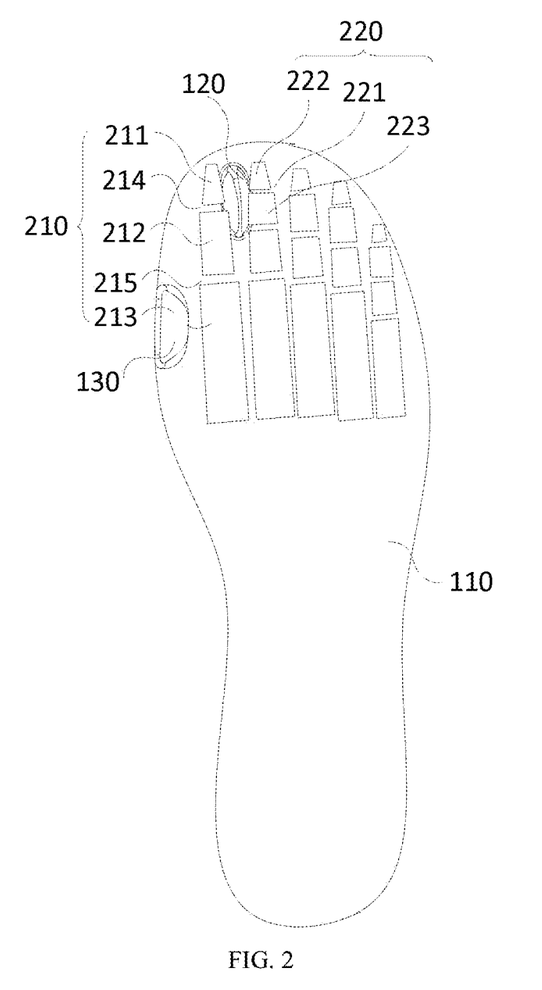
FIG. 2 is a schematic top view of an embodiment of a shoe-pad of the present application.

Referring to FIG. 2, the hallux 210 includes a first bone portion 211, a second bone portion 212, and a third bone portion 213 located a top and a bottom, respectively. A first joint 214 is formed between the first bone portion 211 and the second bone portion 212. A second joint 215 is formed between the second bone 212 and the third bone 213. The first orthotic portion 120 and the second orthotic portion 130 respectively correspond to the outer side of the first joint 214 and the inner side of the third bone portion 213 (a side of two feet opposite to each other is defined as an inner side, and a side of two feet away from each other is defined as an outer side). In this embodiment, the first bone portion 211 is the first distal phalangeal bone of the hallux 210, the second bone portion 212 is the first proximal phalanx of the hallux, and the third bone portion 213 is the first metatarsal bone of the hallux. The first joint 214 is a distal joint of the first proximal phalangeal 212; the second joint 215 is a proximal joint of the first proximal phalangeal 212. In the present embodiment, the front end of the second orthotic portion 130 is aligned with the second joint 215.

Figure 3:
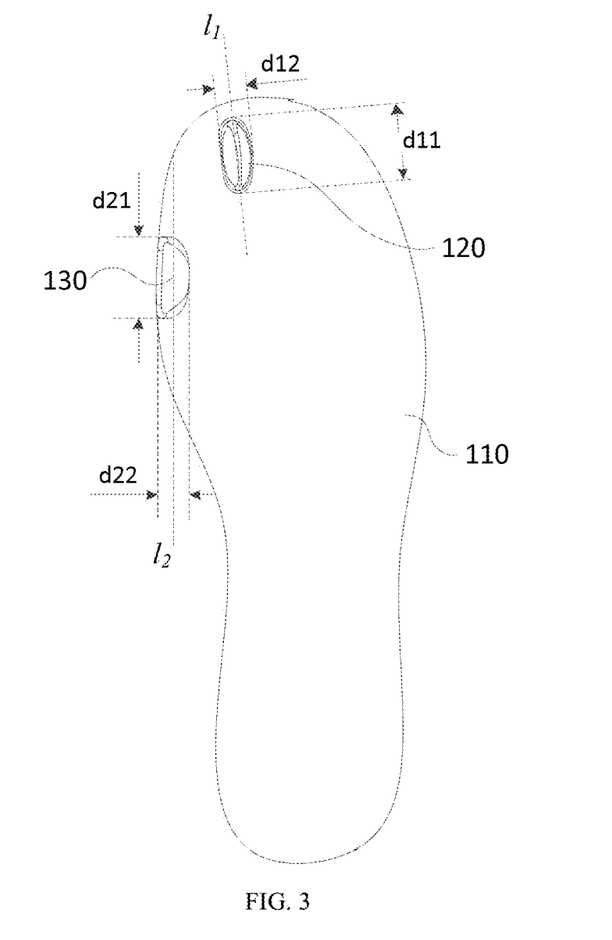
FIG. 3 is a schematic top view of an embodiment of a shoe-pad of the present application.
Figure 4:
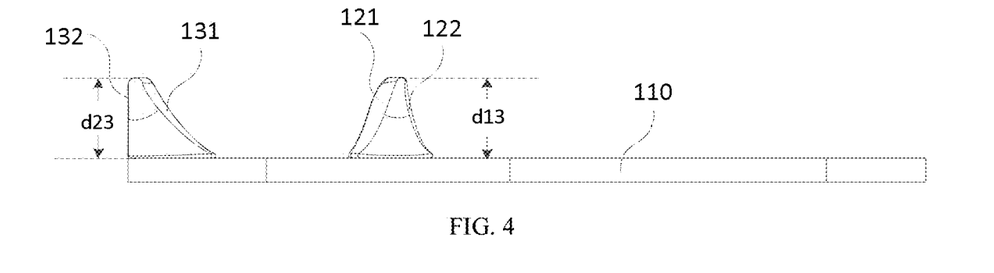
FIG. 4 is a schematic front view of an embodiment of a shoe-pad of the present application.

Referring to FIGS. 3 and 4, the central axis 11 of the first orthotic portion 120 and the central axis 12 of the second orthotic portion 130 are not parallel, and the projections of the first orthotic portion 120 and the second orthotic portion 130 on a width direction (as shown in FIG. 3, d22 refers to the width of the second orthotic portion 130) of the second orthotic portion 130 are not overlapped. The length d11 of the first orthotic portion 120 and the length d21 of the second orthotic portion 130 are 5-25 mm, such as 5 mm, 10 mm, or 25 mm; the width d12 of the first orthotic portion 120 and the width d22 of the second orthotic portion 130 are 10-30 mm, such as 10 mm, 20 mm or 30 mm; the height d13 of the first orthotic portion 120 and the height d23 of the second orthotic portion 130 are 5-20 mm, such as 5 mm, 10 mm, or 20 mm. In this embodiment, the width and height of the first orthotic portion 120 are smaller than or equal to the width and height of the second orthotic portion 130, respectively.

Referring to FIGS. 1 to 4, the first orthotic portion 120 and the second orthotic portion 130 are respectively provided with curved surfaces or oblique surfaces matching with the corresponding hallux 210. Specifically, the first orthotic portion 120 and the second orthotic portion 130 are respectively provided with a first contact surface 121 and a second contact surface 131 corresponding to the hallux 210 for abutting on the hallux 210 respectively. In this embodiment, the first contact surface 121 and the second contact surface 131 are curved surfaces, and the first contact surface 121 and the second contact surface 131 are recessed toward the surface of the shoe-pad body 110, and the radian of the first contact surface 121 is greater than that of the second contact surface 131 and corresponds to the surface radian of the hallux 210, respectively.

The first orthotic portion 120 also corresponds to the inner side of the third joint 221 of the second toe 220. In this embodiment, the third joint is the distal joint 221 of the second mid-section toe bone 223 of the second toe 220 and is located in the joint of the second middle phalanx 223 and the second distal phalanx 222.

The first orthotic portion 120 is further provided with a curved surface or an oblique surface matching with the corresponding second toe 220. Specifically, the first orthotic portion 120 is provided with a third contact surface 122 corresponding to the second toe 220, and the third contact surface 122 is disposed opposite to the first contact surface 121 for abutting with the second toe. In this embodiment, the third contact surface 122 is a curved surface, and the third contact surface 122 is recessed toward the surface of the shoe-pad body 110. The radian of the third contact surface 122 is smaller than that of the first contact surface 121 for corresponding to the surface radian of the second toe 220.

Figure 5A:
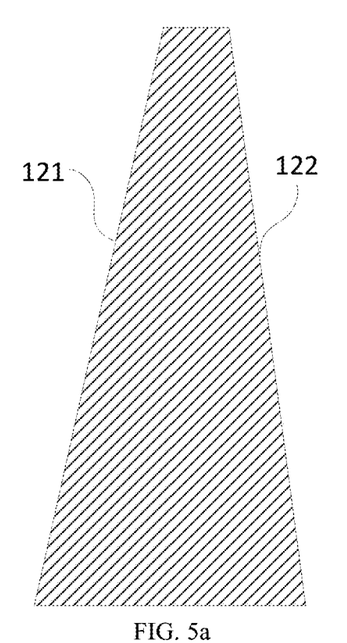
FIG. 5a is a schematic cross-sectional structural view of a first orthotic portion in another embodiment of a shoe-pad of the present application.
Figure 5B:
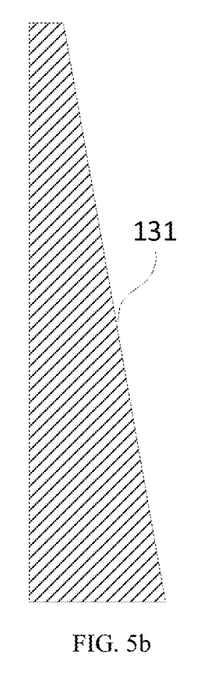
FIG. 5b is a schematic cross-sectional structural view of a second orthotic portion in another embodiment a shoe-pad of the present application.
Figure 6A:
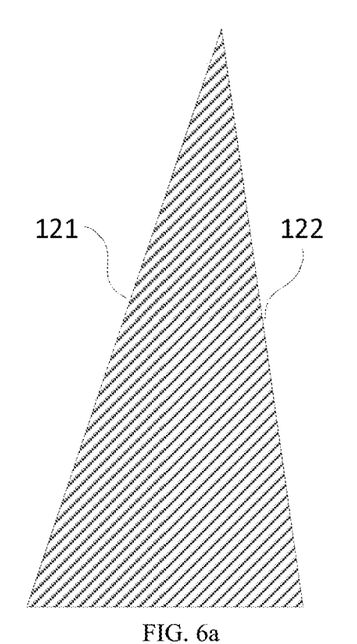
FIG. 6a is a schematic cross-sectional structural view of a first orthotic portion in another embodiment of a shoe-pad of the present application.
Figure 6B:
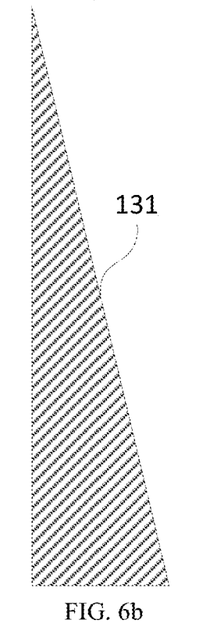
FIG. 6b is a schematic cross-sectional structural view of a second orthotic portion in another embodiment of a shoe-pad of the present application.

In other embodiments, the first contact surface 121, the second contact surface 131, and the third contact surface 122 may also be oblique surfaces. For example, as shown in FIG. 5a and FIG. 5b, the cross section of the first orthotic portion 120 is a trapezoid, the first contact surface 121 and the third contact surface 122 are two oblique sides of the trapezoid, and the oblique angle of the first contact surface 121 (the angle between the contact surface 121 and the surface of the shoe-pad body 110) is smaller than the oblique angle of the third contact surface 122 (the angle between the third contact surface 122 and the surface of the shoe-pad body 110). The cross section of the second orthotic portion 130 is a right-angled trapezoid, and the second contact surface 131 is an oblique side of the right-angled trapezoid. For another example, as shown in FIG. 6a and FIG. 6b, the cross section of the first orthotic portion 120 is a triangle, the first contact surface 121 and the third contact surface 122 are two oblique sides of the triangle, and the oblique angle of the first contact surface 121 is smaller than that of the third contact surfaces 122. The cross section of the second orthotic portion 130 is a right triangle, and the second contact surface 131 is a hypotenuse of the right triangle.

Referring to FIGS. 3 and 4, the second orthotic portion 130 further includes an inner side surface 132, which is disposed opposite to the second contact surface 131, and the inner side surface 132 is aligned with the side surface of the shoe-pad body 110. In this embodiment, the inner side surface 132 is a plane perpendicular to the surface of the shoe-pad body 110. In other embodiments, when the length of the second orthotic portion 130 is longer, the inner side surface 132 may also be an arc surface corresponding to the side surface of the shoe-pad body 110.

Figure 7:
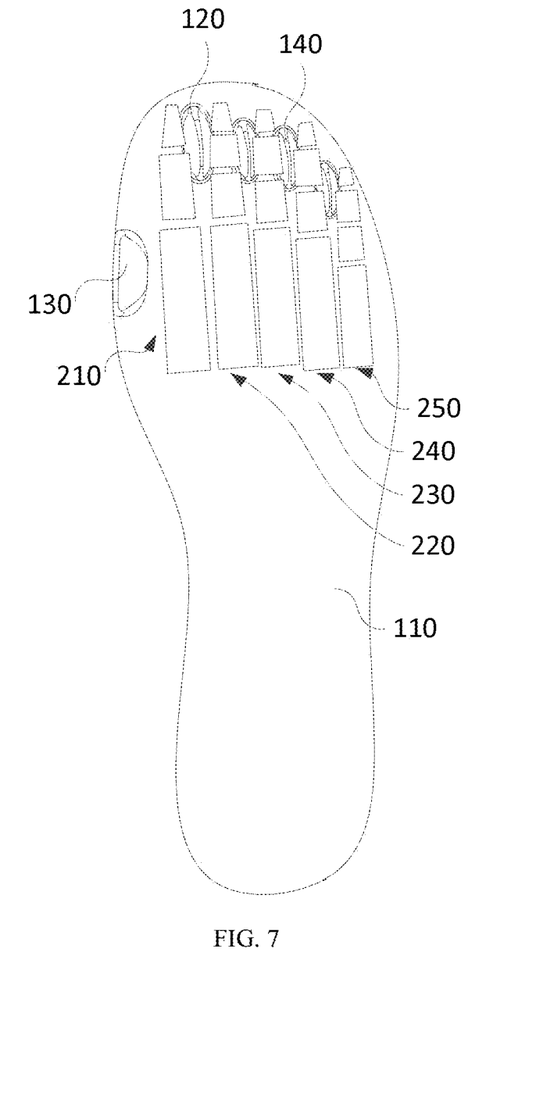
FIG. 7 is a schematic top view of another embodiment of a shoe-pad of the present application.

Referring to FIG. 7, in another embodiment, the shoe-pad 10 may further include a third orthotic portion 140 protruding from the surface of the shoe-pad body 110 and spaced from the first orthotic portion 120, and the third orthotic portion 140 corresponds to the outer side of the second toe 220, the third toe 230 and/or the fourth toe 240.

In this embodiment, the shoe-pad body 110 is provided with three third orthotic portions 140, which are respectively located between the second toe 220, the third toe 230, the fourth toe 240, and the fifth toe 250, and are configured for correcting and preventing the deformities of the second toe 220, third toe 230, fourth toe 240, and fifth toe 250. In other embodiments, one or two third orthotic portions 140 may be further provided on the shoe-pad body.

Figure 8:
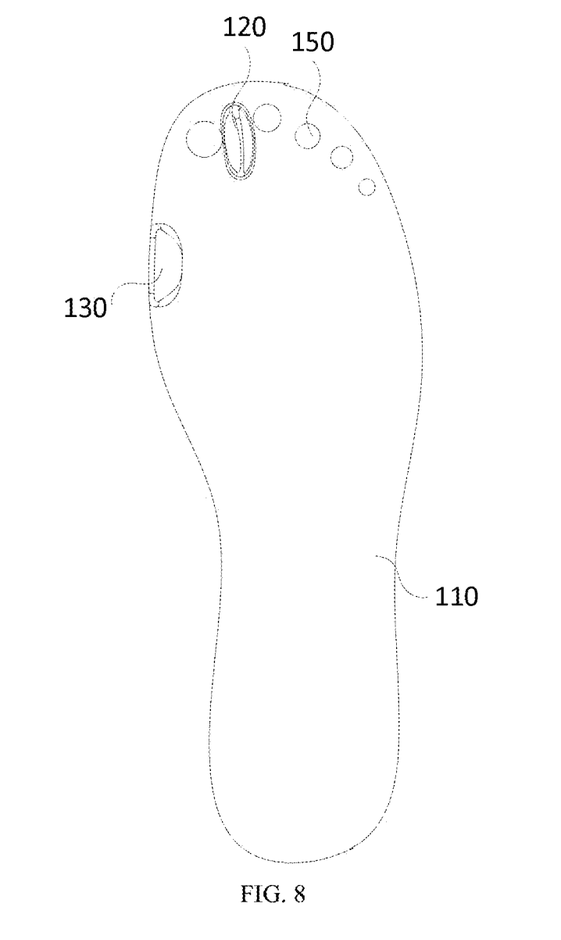
FIG. 8 is a schematic top view of another embodiment of a shoe-pad of the present application.

Referring to FIG. 8, in another embodiment, the shoe-pad 10 further includes a recessed portion 150 provided on the surface of the shoe-pad body 110. The recessed portion 150 corresponds to the hallux 210 or other toes to fit the surface of the toes and increase comfort level.

In other embodiments, the shoe-pad 10 may further include the third orthotic portion 140 and the recessed portion 150 described above.

Figure 9:
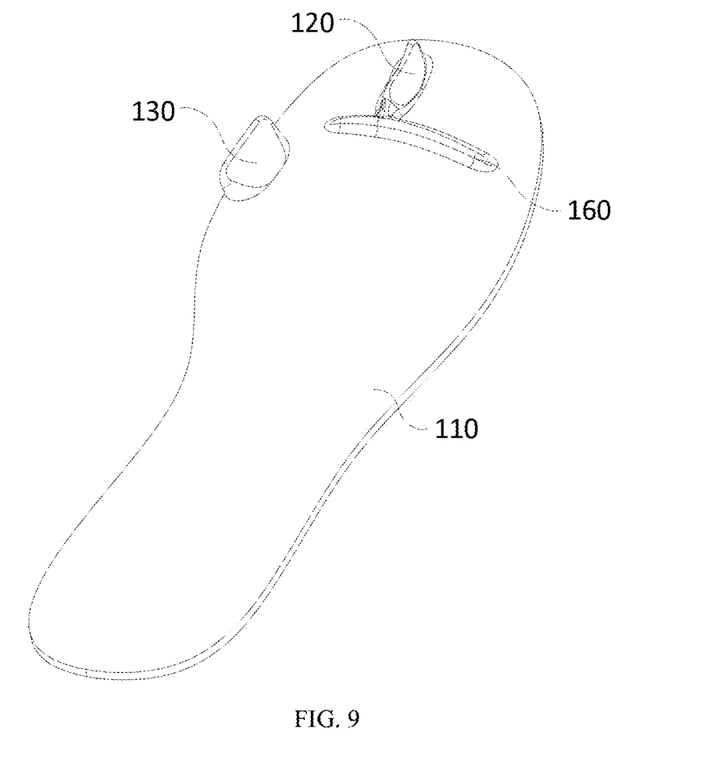
FIG. 9 is a schematic structural view of another embodiment of a shoe-pad of the present application.

Referring to FIG. 9, in another embodiment, the shoe-pad 10 further includes a raised portion 160 provided at the rear end of the first orthotic portion 120. The raised portion 160 is located between the toe and the sole of the foot and configured for limiting the correcting, such that when user is walking or wearing high heels, the foot can be restricted to the rear end of the raised portion 160, thereby the foot is not easily squeezed by the front end of the shoe, which improves comfort of the shoe-pad, and also helps to limit the first orthotic portion 120 and the second orthotic portion 130 always corresponds to the first joint 214 and the third bone 213, respectively.

Figure 10:
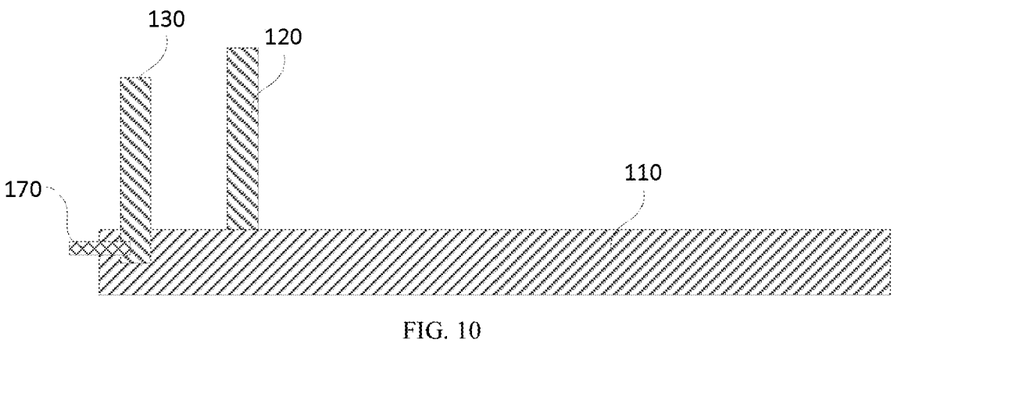
FIG. 10 is a schematic cross-sectional structure view of another embodiment of a shoe-pad of the present application.
Figure 11:
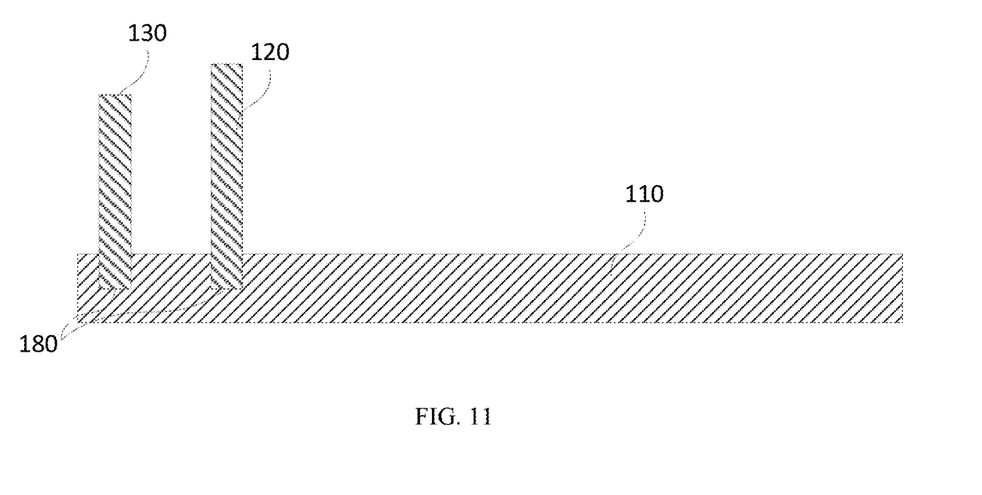
FIG. 11 is a schematic cross-sectional structure view of another embodiment of a shoe-pad of the present application.

Referring to FIG. 10, in another embodiment, at least a part of the first orthotic portion 120 and/or the second orthotic portion 130 extends into the shoe-pad body 110. The shoe-pad 10 includes an adjusting portion 170 disposed on a side of the shoe-pad body 110, and the adjusting portion 170 is connected to the part of the first orthotic portion 120 and/or the second orthotic portion 130 extended into the shoe-pad body 110 to adjust the relative position of the first orthotic portion 120 and/or the second orthotic portion 130 with the shoe-pad body 110. For example, as shown in FIG. 11, a bottom end portion of the second orthotic portion 130 extends into the shoe-pad body 110, and a side of the shoe-pad body 110 corresponding to the second orthotic portion 130 is provided with an adjusting portion 170 connected to the bottom of the second orthotic portion 130. The second orthotic portion 130 can adjust the relative distance between the second orthotic portion 130 and the side of the shoe-pad body 110 through the adjusting portion 170, so as to adapt to different sizes and shapes of the toes and achieve better correction effects.

Referring to FIG. 11, in another embodiment, the shoe-pad body 110 is provided with a groove 180. The first orthotic portion 120 and the second orthotic portion 130 are inserted into the groove 180 to be fixed to the shoe-pad body 110. When it is not necessary to use the first orthotic portion 120 and the second orthotic portion 130, the first orthotic portion 120 and the second orthotic portion 130 can be taken out. The shoe-pad 100 may further include a filling block (not shown in the figure). The shape and size of the filling block is matched with that of the groove 180. After the first orthotic portion 120 and the second orthotic portion 130 are taken out, the filling block fills the groove 180 such that the surface of shoe-pad body 110 is flat.

In other embodiments, the first orthotic portion 120 and the second orthotic portion 130 may also be inflatable members. When the first orthotic portion 120 and the second orthotic portion 130 are not necessary to be used, the first orthotic portion 120 and the second orthotic portion 130 can be contained in the groove 180; and when the first orthotic portion 120 and the second orthotic portion 130 are necessary to be used, the first orthotic portion 120 and the second orthotic portion 130 are inflated to form a prefabricated shape to correct and prevent the deformity of the hallux.

In the present application, the first orthotic portion and the second orthotic portion are spaced from each other on the shoe-pad body, and the first orthotic portion and the second orthotic portion are staggered from each other in a front-back direction, the structure is simple, the production and using are convenient, the hallux valgus can be corrected and prevented without a surgery, and the suffering and financial burden of the patients are reduced.

The embodiment of a shoe provided in the present application includes a first pad and a first orthotic portion and a second orthotic portion protruding from a surface of the first pad and spaced from each other, and the first orthotic portion and the second orthotic portion are staggered from each other in a front-back direction. The shoe is configured for correcting and preventing deformity of the hallux.

Specifically, for the structures of the first orthotic portion and the second orthotic portion, refer to the foregoing shoe-pad embodiments, and details are not described herein again.

In the present application, the first orthotic portion and the second orthotic portion are spaced from each other on the shoe-pad body, and the first orthotic portion and the second orthotic portion are staggered from each other in a front-back direction, the structure is simple, the production and using are convenient, the hallux valgus can be corrected and prevented without a surgery, and the suffering and financial burden of the patients are reduced.

The embodiment of a toe orthotic device, especially a hallux orthotic device provided in the present application includes a second pad and a first orthotic portion and a second orthotic portion protruding from a surface of the second pad and spaced from each other, and the first orthotic portion and the second orthotic portion are staggered from each other in a front-back direction. The hallux orthotic device is configured for correcting and preventing deformity of the hallux.

In the present embodiment, the first orthotic portion is disposed at a side of the toe to be corrected and configured for applying a first orthotic force onto the toe to be corrected. In the present embodiment, the first orthotic force is preferably adapted to fit on the inner side of the hallux, that is, located between the hallux and the second toe; the first orthotic force is a orthotic force to move the hallux to a direction away from the second toe.

The second orthotic portion is disposed at another side of the toe to be corrected and configured to arc-shaped fit to an area to be corrected of the toe to be corrected, to continuously apply a second orthotic force to the area to be corrected. In the present embodiment, the second orthotic portion is preferably adapted to fit on the outer side of the toe, and is preferably located outside the bottom of the toe, and the second orthotic force continuously applies force on the area to be corrected. In addition, the first orthotic force is faced the outer side of the hallux and the second orthotic force is faced the inner side of the hallux.

The first orthotic portion and the second orthotic portion are spaced from each other on a member to be mounted (such as shoe-pad), and the first orthotic portion the second orthotic portion are staggered from each other in a front-back direction. Herein, the first orthotic force and the second orthotic force do not face each other. The first orthotic force acts on the inner side of the upper part of the hallux, and the second orthotic force acts on the outer side of the bottom of the toe. The combination of the first orthotic force and the second orthotic force makes the hallux to be rotated slowly counterclockwise around the middle portion of the hallux. Thereby, the hallux valgus can be corrected over time, and preventing the hallux valgus.

Specifically, for the structures of the first orthotic portion and the second orthotic portion, refer to the foregoing shoe-pad embodiments, and details are not described herein again.

In an embodiment, the toe orthotic device can be arranged on the shoe-pad above mentioned. In other embodiments, the toe orthotic device can be arranged in the shoe, or directly form an orthotic device.

In the present application, the first orthotic portion and the second orthotic portion are spaced from each other on the shoe-pad body, and the first orthotic portion and the second orthotic portion are staggered from each other in a front-back direction, the structure is simple, the production and using are convenient, the hallux valgus can be corrected and prevented without a surgery, and the suffering and financial burden of the patients are reduced.

The aforementioned embodiments are only preferred embodiments of the present application. For one of ordinary skill in the art, according to the thought of the present application, specific implementation modes and application scopes may be modified, and the content of the specification should not be interpreted as any limitation to the present application.

What is claimed is:

1. A shoe-pad configured for correcting and preventing deformity of a hallux, comprising:
   a shoe-pad body, provided with a groove;
   a first orthotic portion; and
   a second orthotic portion;
   wherein the first orthotic portion and the second orthotic portion are protruded from a surface of the shoe-pad body and spaced from each other, and the first orthotic portion and the second orthotic portion are staggered from each other in a front-back direction;
   wherein the first orthotic portion and the second orthotic portion are respectively provided with a first contact surface and a second contact surface corresponding to two sides of the hallux to be corrected for abutting on the hallux to be corrected respectively;
   wherein the first contact surface and the second contact surface are curved surfaces, and the first contact surface and the second contact surface are recessed toward a surface of the shoe-pad body, and a radian of the first contact surface is greater than that of the second contact surface; the first orthotic portion is provided with a third contact surface disposed opposite to the first contact surface, and a radian of the third contact surface is smaller than that of the first contact surface, such that cross sections of the first orthotic portion and the second orthotic portion are gradually decreased from a bottom to a top;
   wherein a central axis of the first orthotic portion and a central axis of the second orthotic portion are not parallel, and directions of the central axis of the first orthotic portion and the central axis of the second orthotic portion are along a length direction of the hallux to be corrected; and
   wherein the first orthotic portion and the second orthotic portion are inflatable members and can be contained in the groove when first orthotic portion and the second orthotic portion are not used.

2. The shoe-pad of claim 1, wherein the first orthotic portion is configured to correspond to an outer side of a first joint formed between a first bone portion and a second bone portion of the hallux to be corrected, and the second orthotic portion is configured to correspond to an inner side of a second joint formed between the second bone portion and a third bone portion of the hallux to be corrected.

3. The shoe-pad of claim 2, wherein a front end of the second orthotic portion is aligned with the second joint.

4. The shoe-pad of claim 1, wherein the first orthotic portion is provided with curved surfaces or oblique surfaces matching with the hallux and a second toe, and the second orthotic portion is provided with a curved surface or an oblique surface matching with the hallux.

5. The shoe-pad of claim 1, wherein the shoe-pad further comprises a third orthotic portion protruding from the surface of the shoe-pad body and spaced from the first orthotic portion, and the third orthotic portion is configured to correspond to an outer side of a second toe, a third toe and/or a fourth toe.

6. A toe orthotic device, comprising: a shoe-pad body, provided with a groove; a first orthotic portion, disposed at a side of a toe to be corrected and configured for applying a first orthotic force onto the toe to be corrected; and a second orthotic portion, disposed at another side of the toe to be corrected and configured to arc-shaped fit to an area to be corrected of the toe to be corrected, to continuously apply a second orthotic force to the area to be corrected; wherein the first orthotic force and the second orthotic force are simultaneously applied to their corresponding areas, and an applying direction of the first orthotic force is deviated and opposite to that of the second orthotic force; wherein the first orthotic portion is provided with a first contact surface configured to be fit to the side of the toe to be corrected, and the second orthotic portion is provided with a second contact surface configured to be fit to the area to be corrected; wherein the first contact surface and the second contact surface are curved surfaces recessed toward a surface of the shoe-pad body, and a radian of the first contact surface is greater than that of the second contact surface; the first orthotic portion is provided with a third contact surface disposed opposite to the first contact surface, and a radian of the third contact surface is smaller than that of the first contact surface, such that cross sections of the first orthotic portion and the second orthotic portion are gradually decreased from a bottom to a top; and wherein a central axis of the first orthotic portion and a central axis of the second orthotic portion are not parallel, and directions of the central axis of the first orthotic portion and the central axis of the second orthotic portion are along a length direction of a hallux of the toe to be corrected; and wherein the first orthotic portion and the second orthotic portion are inflatable members and can be contained in the groove when first orthotic portion and the second orthotic portion are not used.

7. The toe orthotic device of claim 6, wherein a radian of the first contact surface is greater than that of the second contact surface.

8. The toe orthotic device of claim 6, wherein the first orthotic portion and the second orthotic portion are disposed apart from each other on a member to be mounted, and the first orthotic portion and the second orthotic portion are staggered from each other in a front-back direction.

9. The toe orthotic device of claim 6, wherein the first orthotic portion is arranged at an inner side of the hallux of the toe to be corrected, and the second orthotic portion is arranged at an outer side of the hallux of the toe to be corrected.

10. The toe orthotic device of claim 9, wherein the first orthotic force is applied onto the outer side of the hallux and the second orthotic force is applied onto the inner side of the hallux of the toe to be corrected.

* * * * *